United States Patent [19]
Slavicek et al.

[11] Patent Number: 5,571,672
[45] Date of Patent: Nov. 5, 1996

[54] GYPSY MOTH GENOTYPE ASSAY

[75] Inventors: James M. Slavicek, Dublin; Karen J. Garner, Delaware; David E. Schreiber, Columbus, all of Ohio

[73] Assignee: The United States of America as represented by the Secretary of Agriculture, Washington, D.C.

[21] Appl. No.: 308,894

[22] Filed: Sep. 20, 1994

[51] Int. Cl.$^6$ ............................ C12Q 1/68; C12P 19/34; C07H 21/02; C07H 21/04
[52] U.S. Cl. ........................... 435/6; 435/91.2; 536/23.1; 536/24.31; 536/24.33
[58] Field of Search ................ 435/6, 91.2; 536/23.1, 536/24.31

[56] References Cited

U.S. PATENT DOCUMENTS

| | | | |
|---|---|---|---|
| 4,889,818 | 12/1989 | Gelfand et al. | 435/194 |
| 4,965,188 | 10/1990 | Mullis et al. | 435/6 |
| 5,043,272 | 8/1991 | Hartley | 435/91 |
| 5,079,352 | 1/1992 | Gelfand et al. | 536/23.2 |

OTHER PUBLICATIONS

S. M. Bogdanovicz, et al., "Asian Gypsy Moths (Lepidoptera: Lymantriidae) in North America: Evidence from Molecular Data," *Ann. Entomol. Soc. Am.* 86(6):710–715, 1993.

S. Hiremath, et al., "Purification and Characterization of Vitellogenin from the Gypsy Moth, *Lymantria dispar*," *Insect Biochem. Molec. Biol.* 22(6):605–611, 1992.

S. Tanaka, et al., "Developmental Landmarks and the Activity of Juvenile Hormone and Juvenile Hormone Esterase During the Last Stadium and Pupa," *J. Insect Physiol.* 35(11):897–905, 1989.

Haymer, D. Resolution of populations of Meditteranean fruit fly at the DNA level using random primers for the polymerase chain reaction Genome 37(2) pp. 244–248, May 13,1994.

*Primary Examiner*—Stephanie W. Zitomer
*Assistant Examiner*—Dianne Rees
*Attorney, Agent, or Firm*—Janet I. Stockhausen; M. Howard Silverstein; John D. Fado

[57] ABSTRACT

A method for determining the genotype of a gypsy moth is disclosed. This method begins with the steps of isolating genomic DNA from a candidate gypsy moth, exposing that DNA to an oligonucleotide primer selected from the group consisting of SEQ ID NOs:3, 4, 5, 6, 7 or the complement thereof and sequences sufficiently similar to SEQ ID NOs:4 and 5 or the complement thereof under conditions permitting amplification of the genomic DNA, and comparing the amplified DNA with amplified DNA produced by control samples. A genotype identity is assigned to the candidate moth according to which control sample has amplified fragments similar to those in the candidate sample. A method for obtaining DNA primers for determining the genotype of candidate moths is also disclosed. This method comprises the steps of obtaining the DNA sequence of fragments FS-1, FS-2, or FS-3 from both the Asian moth DNA and North American/European moth DNA and analyzing the sequences to obtain primers capable of priming an amplified product of different size in Asian and North American/European gypsy moth DNA samples.

12 Claims, 5 Drawing Sheets

FIG. 4

SEQ. ID NO. 4-FS1U33 5' GGATGGTG GGTGTCGTT 3'>

```
                    10         20         30         40         50
SEQ. ID NO.1 - ASIAN   GGACCCAACC CGTCTGATCA GYATGGTATA GCGGATGGTG GGTGTCGTTA
SEQ. ID NO. 2- N. AM.  GGACCCAACC CGTCTGATCA GTATGGTATA GGGGATGGTG GGTGTCGTTA 60         70         80         90        100
         ASIAN   ARGACGTTTA AAATGTATAT AACATCAATG TCAGAGAAAG AAAACTCAAC
         N. AM.  AAGACGTTTA AAATGTATAC ---------- ---------- ----------

110        120        130        140        150
         ASIAN   ATAAAGTATG CCAACTCGWC TGRCYAKCTT GATATAGTAG GTCAATTKCT
         N. AM   ---------- ---------- ---------- ---------- ----------

160        170        180        190        200
         ASIAN   ACCCCATTAT GGAAGGAGGT TCAAGRGCAG CACTGAGACA GAGATTGAAC
         N. AM   ---------- ---------- -----AGCAG tACTGAGACA GAGATTGAAC 210        220        230        240        250
         ASIAN   TGTGATCATG AATTATCAGG ATCAGATGAA TCTAAAACAA ATACCTAACC
         N. AM   TGTGATCATG AATTATCAGG ATCAGATGAA TCTAAAACAA ATACCTAACC 260        270        280        290        300
         ASIAN   AAAAATTGGA ATAAACTAAT TTTAYGGTAA TTTTAAGGYT AATAATCATA
         N. AM   AAAAATTGGA ATAAMCTAAT TTTATGGTAA TTTTAAGGCT AATAATCATA 310        320        330        340        350
         ASIAN   ATTCATAAGC AAATTATTCC ACAACATCTR ATCATCAACC AACCGCCYCA
         N. AM   ATTCATAAGC AAATTATTCC ACAACATCTA ATCATCAACC AACCGCCTCA
                         SEQ. ID NO. 5 - FS1L32<3' GTAGATTAGT AGTTGGTTGG 5'

360        370        380        390        400
         ASIAN   AACAACAGAA CAAATRAGCA ACACGTCGAT GTCCTCTCCG GAATGACAAT
         N. AM   AACAACAGAA CAAATAAGCA ACACGTCGAT GTCCTCTCCG GAATGACAAT 410        420        430        440        450
         ASIAN   GATTATTGTA ACAGCCTCAT AAACCGGCAT TATTGTGAGC GCACTGTATT
         N. AM   GATTATYGTA RCAGCCTCAT AAACCGGCAT TATTGTGAnn GnACTGTATT 460        470        480        490        500
         ASIAN   TATACGCCAT AGCAATTATC GGTCGTAACT GCCGCATCGA TCTTCGTCGA
         N. AM   TATAC-nnAT AGCAATTATC GGTCGTAACT GCCGCATCGA TCTTCGTCGA 510        520        530        540        550
         ASIAN   TAATTGCCTT GTGAAACATG AGTTATTGTT CCATCTGAAC TAATTAGTGT
         N. AM   TAATTGCCTT GTGAAACATG AGTTATTGTT CCATATGAAC TAATTAGTGT 560        570        580        590        600
         ASIAN   ATGTTATTAG GTTAAGGGTG ACATTTTGAA GTYATACTAC TTCTGACACT
         N. AM   ATGTTATTAG GTTAAGGGTG ACATTTTGAA GTTATACTAC TTCTGACACT 610        620        630        640        650
         ASIAN   TTAGGGRAAA AACATCATCG GGCCGACCAC TGAAGACAAG TTACTCTGCA
         N. AM   TTAGGGnAAA AACATCATCG GGCCGACCAC TGAAGACAAG TTACTCTGCA 660        670        680        690
         ASIAN   CCGATGGTCG GCTCAACGAT GAAGGCGACG TGTCACGGTT GGGTCC
         N. AM   CCGATGGTCG GCTCAACGAT GAAGGCGACG TGTCACGGTT GGGTCC
```

GYPSY MOTH GENOTYPE ASSAY

FIELD OF THE INVENTION

In general, the field of the present invention is assays designed to detect different strains of gypsy moths. In particular, the field of the present invention is DNA diagnostic assays designed to identify the Asian and European/North American strains of the gypsy moth and Asian-European/North American gypsy moth hybrids.

BACKGROUND OF THE INVENTION

The North American gypsy moth (*Lymantria dispar*) originated in France and was first introduced into Bedford, Mass. in 1869. Since that time *L. dispar* has spread through the New England area and into the states of New York, Pennsylvania, Ohio, Michigan, Delaware, Maryland, and North Carolina. These states define the generally infested area within the U.S. In addition, localized gypsy moth infestations have been identified and eradicated from nearly all of the remaining states in the U.S.

The gypsy moth strain present in the generally infested area is termed the European or North American strain. However, other gypsy strains are present in the world. Strains in which female moths have flight capability are of greatest concern due to the potential rapid spread of the strain from the point of introduction. The Asian strain is one example of a strain capable of flight. In contrast to the Asian strain, females of the European/North American strain are not capable of flight.

Recent introductions of the Asian gypsy moth strain in the U.S. have caused great concern. In addition to flight capability, the Asian strain has greater host range than the European/North American strain. Consequently, the potential economic losses from an Asian gypsy moth infestation measures in the billions of dollars. Asian gypsy moth introductions in the Pacific Northwest and North Carolina have resulted in eradication efforts costing approximately 15 million dollars. Additionally, international commerce could be affected.

Asian and European/North American strains of gypsy moth cannot be distinguished accurately by morphological differences when the samples are collected in pheromone traps due to the poor physical condition of the specimens. Therefore, an improved method of distinguishing between Asian and European/North American gypsy moths is needed.

SUMMARY OF THE INVENTION

The present invention is a method for determining the genotype of a candidate gypsy moth. The method comprises the first step of isolating genomic DNA from a candidate gypsy moth. This DNA is exposed to an oligonucleotide primer selected from the group consisting of SEQ ID NOs:3, 4, 5, 6, 7 and complements thereof and oligonucleotides sufficiently similar to SEQ ID NOs:4 and 5 or complements thereof such that identical amplification products are obtained. The primer or primers are exposed to the genomic DNA under conditions permitting amplification of the genomic DNA. The amplification products of the candidate gypsy moth DNA are compared with amplified DNA products produced by exposing DNA obtained from Asian, North American/European and hybrid gypsy moths to the same primer or primer pair that the control DNA was exposed to. A genotype identity is assigned to the candidate moth according to which control sample has amplified fragments similar to those produced in the candidate sample.

In a preferred form of the present invention, the comparison is by electrophoresing the amplified DNA.

In a particularly preferred form of the present invention, the oligonucleotide primer is SEQ ID NO:3 or the complement thereof and the amplified DNA from the control Asian moths is approximately 700 bp and from control North American/European moths is approximately 590 bp.

In another preferred form of the present invention, the oligonucleotide primer is SEQ ID NO:6 or the complement thereof and the amplified DNA from the control North American/European moths is approximately 800 bp. The Asian moth samples do not produce this approximately 800 bp fragment.

In another preferred form of the present invention, the oligonucleotide primer is SEQ ID NO:7 or the complement thereof and the amplified DNA from the control North American/European moths is approximately 600 bp. The control Asian moth samples do not produce this 600 bp piece.

In another preferred form of the present invention, the oligonucleotide primers are SEQ ID NOs:4 and 5 or the complements thereof and the amplified DNA from control Asian moths is approximately 312 bp and from control North American/European moths is approximately 207 bp.

The present invention is also a method of obtaining DNA primers for determining the genotype of a candidate moth. This method comprises the steps of obtaining genomic gypsy moth DNA from Asian and North American/European moths and obtaining fragment FS-2 or FS-3 from both Asian DNA and North American/European DNA by exposing the DNA to primers selected from the group consisting of SEQ ID NOs:6 and 7. The DNA sequence of the fragments is analyzed to obtain primers capable of priming an amplified product of different size in Asian and North American/European gypsy moth DNA samples.

The present invention is also a method of obtaining DNA primers for determining the genotype of a candidate moth by analyzing the sequence of diagnostic fragment FS-1 obtained from both Asian and North American/European gypsy moths to obtain primers capable of priming an amplified product of different size in Asian and North American/European gypsy moth DNA samples.

The present invention is also a purified preparation of an oligonucleotide with the DNA sequence of either SEQ ID NO:4 or SEQ ID NO:5 or complements thereof.

The object of the present invention is to identify Asian, European, and hybrid Asian-European/North American gypsy moths.

Another object of the present invention is to identify Asian, North American/European, and hybrid Asian-North American/European gypsy moths in an assay depending on sequence differences found in nuclear DNA.

Another object of the present invention is to identify Asian, European/North American, and hybrid Asian-North American/European moths in an assay using electrophoretic analysis of PCR fragments.

It is a feature of the present invention that the assay is quick and reproducible.

It is another feature of the present invention that primers can be obtained by analysis of fragments FS-1, FS-2, and FS-3 which are obtained by amplifying Asian gypsy moth DNA and North American/European gypsy moth DNA by exposing the DNA to primers selected from the group consisting of SEQ ID NOs:3, 6, and 7 or complements thereof.

Other objects, advantages, and features of the present invention will become apparent upon examination of the specification, drawings, figures, and claims of the present application.

DESCRIPTION OF THE DRAWINGS

FIG. 4 is a comparison of the DNA sequence of the FS-1 fragment obtained from Asian and North American/European gypsy moths.

DESCRIPTION OF THE INVENTION

1. In General

Figure 1:
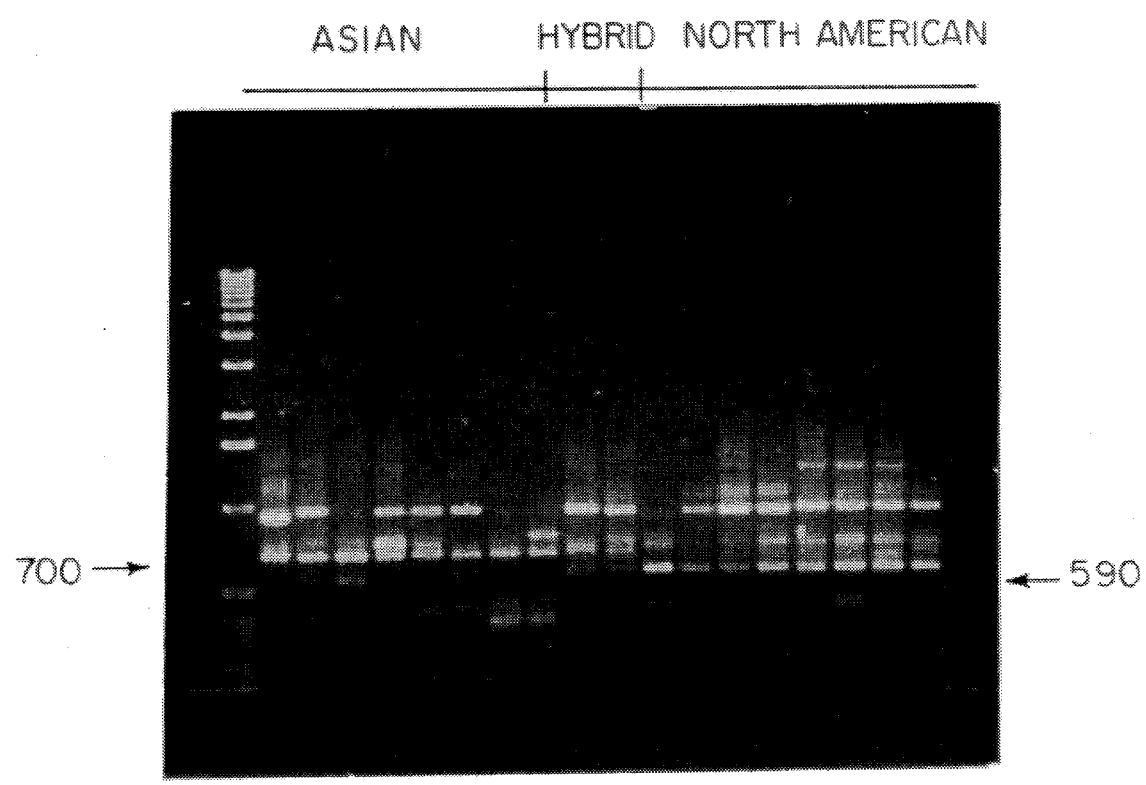
FIG. 1 is a photograph of an agarose gel showing electrophoresis of amplified DNA products created using gypsy moth genomic DNA and primer FS-1.

The present invention is a nuclear-DNA-based diagnostic assay that provides a means to differentiate between the Asian and European/North American strains and identify individual moths that are Asian-European/North American hybrids. The assay is based on previously unknown DNA sequence divergence between the Asian and European/North American strains. This divergence was elucidated by our identification of randomly amplified polymorphic DNAs (RAPDs) that are conserved within and unique to the Asian and North American/European gypsy moth strains. RAPD primers are 10 bp primers that are designed to be used individually, as opposed to the usual primer pair. The RAPD primers that we have identified are capable of priming both ends of a diagnostic fragment.

As the Examples below describe, a library of RAPD primers was purchased from Operon Technologies, Inc., 1000 Atlantic Avenue, Alameda, Calif. 94501, and exposed under appropriate amplification conditions to gypsy moth genomic DNA. The desired end-product of the RAPD assay was the observation of an amplified DNA fragment of defined length that was present in one gypsy moth strain and absent in the other. These fragments would be generated through the use of an individual defined DNA RAPD oligonucleotide as a primer in the polymerase chain reaction.

We have identified three specific RAPD primer sequences (primer FS-1, primer FS-2, and primer FS-3) that generate diagnostic fragment markers. We term the diagnostic fragments FS-1, fragment FS-2, and fragment FS-3. These markers and the assay used to generate them are described in detail below. The specific RAPD primers are described below and in SEQ ID NOs:3, 6, and 7. An improved set of primers designed to generate the FS-1 fragments are described below and in SEQ ID NOs:4 and 5.

The present invention is also a method of identifying other improved PCR primers capable of generating fragments FS-1, fragment FS-2, and fragment FS-3. These marker fragments can be cloned and sequenced. The nucleotide sequence information can be used to design new oligonucleotide primers of greater length than the RAPD primers, which are 10 nucleotides in length. The longer primers allow the use of more stringent PCR reaction conditions, which constitutes an improved assay with more sensitivity.

As described below, we have generated and tested primers of greater than 10 nucleotides that were derived from the DNA sequence of the FS-1 fragment. An identical analysis can be performed on the FS-2 and FS-3 fragments.

2. Obtaining Gypsy Moth DNA from a Candidate Moth

The first step of the present invention is obtaining genomic DNA from a candidate moth. The Examples below described a preferred method for obtaining gypsy moth DNA. Preferably, the purified DNA is further purified by elution over a DNA purification column such as an ELUTIP-D column (Schleicher and Schuell).

The DNA amplification method can be used with DNA obtained from almost any type of gypsy moth tissue, even if the specimen is in poor condition. In most cases the method is preferably used to analyze dried adult male specimens collected in pheromone traps. We have successfully amplified DNA from dried, frozen, or ethanol-preserved adult tissue, frozen or ethanol-preserved larvae, and unpreserved or ethanol-preserved eggs.

Crude lysates of tissue can be used successfully with the FS-1-U33 and FS-1-L325 primers (SEQ ID NOs:4 and 5). For best results, the RAPD primers (SEQ ID NOs:3, 6, and 7) should be used with purified DNA.

Adult tissue and egg DNA preparations can be purified by digestion, phenol extraction, chloroform extraction, and ethanol precipitation followed by resuspension, RNAse treatment and an additional phenol extraction, chloroform extraction, and ethanol precipitation. Larval DNA usually requires further purification with an Elutip-D column.

3. Exposing the Candidate DNA to Diagnostic Primers

The next step of the present invention is to expose the candidate DNA to primers known to amplify distinguishable marker fragments. Preferably, these primers have a DNA sequence identical to SEQ ID NOs:3, 6, and 7. These primers may be most easily obtained by in vitro synthesis. Primers can be purchased from one of many companies who specialize in custom DNA synthesis, or they can be synthesized using in-house facilities.

Each of these primers may be used individually to generate diagnostic DNA fragments with Asian moth DNA, North American/European moth DNA, and Asian-North American/European hybrid DNA. The examples below disclose preferable reaction conditions for PCR and the size of fragments generated by control samples. Those of skill in the art will know that the PCR conditions are somewhat flexible and that other general PCR techniques would also be suitable. When optimizing PCR reactions, users should begin with the parameters described in the methods below. If amplification is unsuccessful, the most common adjustments made are usually to change the annealing temperature, and to vary the concentrations of DNA, magnesium, primers, and/or Taq polymerase.

Most preferably, primers with a sequence sufficiently similar to SEQ ID NOs:4 and 5 would be used together. SEQ ID NOs:4 and 5 have been obtained from sequenced fragment FS-1 and are designed to optimize the assay by allowing a more stringent PCR reaction. By "sufficiently similar" we mean that the sequence is similar enough to SEQ ID NOs:4 and 5 to result in the amplification of fragments of the same size. The primers produce a 312 bp fragment with Asian moth DNA and a 207 bp fragment with North American/European moth DNA. Primers identical to SEQ ID NOs:4 and 5 are preferable, but a minor nucleotide substitution or change might also result in a primer that is suitable, especially if the nucleotide change is at nucleotide 9, 10 or 11. It is important that the nucleotides on the 3'end of the oligonucleotide primer be identical to those described in SEQ ID NOs:4 and 5.

To determine whether or not a primer is sufficiently similar to SEQ ID NO:4 or 5, one would construct the candidate primer and expose it to either Asian or North American/European moth DNA under conditions suitable for DNA amplification. Amplification of a fragment of the appropriate size (approximately 312 bp for the Asian sample and approximately 207 bp for the North American/European sample) indicates that the candidate primer is sufficiently similar.

4. Evaluating the Amplification Products

Once the amplification of the genomic DNA has taken place, the next step is to evaluate the amplification products. Typically, one would electrophorese the DNA amplification products from a candidate moth on an electrophoretic gel and examine the size of the amplification products. This size should be compared to amplification products known to result from control moths. The Examples below disclose amplification products resulting from Asian moth DNA, North American/European moth DNA, and hybrid moth DNA.

For example, if one were to amplify the genomic DNA from a candidate moth with a primer identical to SEQ ID NO:3 (primer FS-1), one would examine the amplified DNA for the presence of either an approximately 700 bp fragment or an approximately 590 bp fragment. If the 700 bp fragment exists, then the moth is an Asian strain. If the 590 bp fragment exists, then the moth is a North American/European strain. If both fragments exist, then the moth is a hybrid.

By "approximately 700 bp or 590 bp" we mean that the resolution obtainable with agarose gel electrophoresis is accurate to within 5-10% of the actual fragment size. The actual size of the Asian FS-1 fragment determined from sequence analysis of four moths is 696 bp in three individuals and 697 bp in one individual. The actual size of the North American FS-1 fragment is 590 bp in one moth and 591 bp in another moth. Other slight variants in size may exist but have not been detectable by agarose gel electrophoretic analysis of hundreds of individuals.

Similarly, a candidate sample amplified with SEQ ID NO:6 (primer FS-2) should result in an amplified band of approximately 800 bp if the moth is a North American/European strain. An Asian moth will not contain this fragment.

If the primer SEQ ID NO:7 (FS-3) is used, the sample should be examined for the presence of an approximately 600 bp fragment which is present only in the North American/European samples. If primers SEQ ID NOs:4 and 5 (FS1-U33 and FS1-L325) are used, a fragment of approximately 312 bp will appear in the Asian sample and approximately 207 bp in the North American/European sample. Hybrid moths will contain both fragments.

Of course, those of skill in the art will realize that other bands might also appear in the amplification products and these assays are most properly done side by side with control samples. It is important to stress that positive controls consisting of known Asian, North American/European, and hybrid moth DNA samples are preferably analyzed during each experiment. Enough positive control samples should be run so that they can be included in each gel loading and so be viewed side-by-side with the unknown samples.

In addition, negative control reactions are preferably included whenever possible when PCR is performed. These should consist of PCR reactions with no DNA added, to rule out contamination of the PCR reagents. If possible, mock DNA preparations with no moth tissue added should also be analyzed to rule out sample contamination during DNA preparation.

Those of skill in the art will realize that previously-amplified DNA can easily contaminate DNA preparation and amplification reagents. It is best to have a separate clean work area and dedicated equipment for DNA preparation and PCR reaction set-up. Gel analysis of the amplification should be carried out elsewhere.

5. Obtaining Other Suitable Primers

The present invention is also a method of obtaining other primers suitable for producing diagnostic fragments. The Examples below disclose a method of analyzing the sequence of fragment FS-1 to obtain improved primers.

We observed that RAPD primer FS-1 amplified an approximately 700 bp fragment in Asian moths and an approximately 590 bp fragment in North American/European moths, as well as several other fragments that did not correlate with geographic origin. We wished to design improved, longer primers that were locus-specific. With longer primers the PCR reactions can be performed with higher annealing temperature. Therefore, the amplification of non-diagnostic fragments is reduced or eliminated. A preferred primer size is between 16 and 20 nucleotides.

In addition, the primers were selected so that the length of the amplified fragments would be short enough (shorter than 400 bp) so that amplification could be successful on badly degraded DNA samples, yet long enough (longer than 200 bp) so that the fragments could be resolved using agarose gel electrophoresis rather than polyacrylamide gel electrophoresis, which is more labor-intensive and time-consuming.

We cloned and sequenced the two diagnostic fragments and observed that the sequences were nearly identical except that the 590 bp fragment had a single deleted region relative to the 700 bp fragment. Comparison of the two sequences showed us several areas of the fragment which were suitable for the design of improved primers. The primers were selected in the regions flanking the deleted region, and were designed to match sequences where no mismatches were seen between the two sequences. In addition, the primers were selected so that the length of the amplified fragments would be suitable, as described above. Finally, the selected primers were analyzed using the computer program OLIGO, version 4.0 for Macintosh, written by Wojciech Rychlik, published by National Biosciences, Inc., 3650 Annapolis Lane, Plymouth, Minn. 55447. This program selects primers with compatible annealing temperatures and also analyzes primer pairs for possible problems such as internal secondary structure, self-annealing or inter-primer annealing. Based on a combination of our criteria mentioned above and the results of the computer analysis, we selected the locus-specific primers FS-1-U33 and FS-1-L325. Other appropriate primer pairs might also exist.

A similar analysis can be performed with the fragments amplified by primers FS-2 and FS-3. In both these cases only one fragment size is seen so the selection of locus-specific primers will depend mainly on the computer analysis.

EXAMPLES

1. Materials and Methods

DNA Preparation

Grind buffer: 10 mM Tris-Cl pH 7.5, 60 mM NaCl, 10 mM EDTA. Autoclave ~20 ml aliquots and store at room temperature.

Post-grind buffer: 200 mM Tris-Cl pH 9.0, 30 mM EDTA, 2% Sodium dodecyl sulfate (SDS). Autoclave ~20 ml aliquots and store at room temperature.

Proteinase K: Stock is 10 mg/ml in water. Not autoclavable. Store aliquots in the freezer. 3.0 M sodium acetate, pH 4.8 to 5.2

We also used buffered phenol, pH 7 to 8; Chloroform/isoamyl, alcohol, 24:1; Ethanol, 100%; and ELUTIP-D (Schleicher and Schuell) or similar DNA clean-up columns.

RNase: Stock is 10 mg/ml in 10 mM Tris-Cl pH 8.0, 15 mM NaCl. Inactivate DNAse by boiling for 10 minutes and allowing the solution to cool slowly to room temperature. Store aliquots in the freezer.

Polymerase Chain Reaction

DNA samples: For best reproducibility with RAPD PCR, DNA samples were thoroughly purified and used at similar concentrations. PCR performed with extended primers should be effective over a wide range of DNA concentrations. DNA that is contaminated with interfering impurities may be usable following dilution.

Taq DNA polymerase: Perkin-Elmer or Boehringer Mannheim Taq DNA polymerase, supplied at 5 units per microliter.

Buffer, RAPD PCR: 10X=500 mM KCl, 100 mM Tris-Cl (pH 9.0 at 25° C.), 20 mM $MgCl_2$, 1% Triton X-100.

Buffer, locus-specific PCR: 10X=500 mM KCl, 100 mM Tris-Cl (pH 9.0 at 25° C.), 1% Triton X-100.

$MgCl_2$ was added separately or included in the 10X buffer to a final concentration of 1.0–3.0 mM. Titration of the magnesium concentration may be necessary to obtain optimal results for each primer batch. Buffer and magnesium stocks were stored at −20° C.

Deoxynucleotide triphosphates: Promega or Perkin-Elmer brand, supplied separately and mixed 1:1:1:1 to make a convenient stock concentration, such as 5 mM. This diluted stock can be frozen for several weeks.

Primers: Primers were usually supplied lyophilized and resuspended in water, quantitated by UV spectrophotometry, and diluted to 5 or 10 mM. Long-term storage is at −80° C. and aliquots were stored at −20° C. Primers are commercially available. RAPD primers were purchased as kits from Operon Technologies, Inc., 1000 Atlantic Avenue, Alameda, Calif. 94501. Locus-specific primers were purchased from one of many companies specializing in custom DNA synthesis, such as Biosynthesis, Inc., P.O. Box 28, Lewisville, Tex. 75067-0028, or Bioserve Biotechnologies, 1050 West Street, Laurel, Md. 20707.

Water: Water was reverse osmosis-treated and purified using a Milli-Q system. ~10 ml aliquots were autoclaved and stored at room temperature.

Mineral oil: "Top Care" heavy mineral oil, a local drugstore brand, was used. ~3 ml aliquots were autoclaved and stored at room temperature.

Reaction tubes: PGC Scientifics, Inc. tubes, 0.5 ml snap seal flat top type, catalog #16-8105-03 were used.

Pipet tips: US Scientific Plastics brand catalog #1010-1000 ("natural metal-free tip") pipet tips were used.

Agarose Gel Electrophoresis

Agarose: Bio-Rad high-strength analytical grade agarose, catalog number 162-0125 was used.

TBE buffer, 1X:0.089 M Tris base, 0.089 M boric acid, 0.002 M EDTA.

Methods

Preparation of gypsy moth DNA was adapted from Ish-Horowicz, et al., (1979) Cell 18, 1351–1358. Specifically, DNA isolation and extraction were as follows:

An insect was placed in a glass homogenizer and 1.5–2 ml of grind buffer was added. (More or less may be used based on the size and dryness of the sample—Ish-Horowicz recommends 250 ml buffer per 100 mg insect weight.) The sample was ground until no further breakdown of the tissue was seen. The homogenized tissue was poured into a phenol-resistant centrifuge tube (for example, a 15 ml polypropylene conical Corning tube). An equal volume of post-grind buffer was added to the homogenizer and the remaining homogenate was rinsed into the centrifuge tube. Proteinase K was added to a final volume of 200 mg/ml. The samples were incubated at 50°–55° C. overnight, or at least 4 hours.

3.0 M sodium acetate equal to $\frac{1}{10}$ of the sample volume was added to the samples. An equal volume of phenol was added to the DNA solution and mixed gently for 10 minutes. The samples were centrifuged for 10 to 20 minutes at 2000 rpm. The upper layer (DNA) was removed to a clean tube. An equal volume of chloroform/isoamyl alcohol was added to the DNA and mixed gently for 5 minutes and centrifuged again for 5 minutes. The upper DNA layer was removed to a clean centrifuge tube, one that will tolerate centrifugation at 10,000 rpm.

To precipitate the DNA, 2.5 volumes ethanol was added. (The solution already contained sufficient salts.) The solution was chilled at −20° C. for at least 2 hours. The solution was centrifuged at 10,000 rpm for 30 minutes and the ethanol supernatant was carefully poured off. The pellet was dried by standing the tube upside down or by recentrifuging briefly and carefully removing the remaining trace of ethanol with a thin-tipped pipet or pipet tip. When the pellet was completely dry, it was resuspended in 200–300 ml water or TE. The DNA was resuspended overnight if possible.

The DNA obtained by this method often will not amplify well, particularly if the DNA is obtained from larvae. To further purify DNA, we used a DNA purification column such as an ELUTIP-D column from Schleicher and Schuell, and followed the manufacturer's procedure.

After the DNA was ethanol precipitated, it was resuspended in 200 microliters of water and allowed to dissolve overnight.

The DNA was then treated with RNase to remove contaminating RNA. RNase was added to a final concentration of 50 micrograms per ml and the solution was incubated for 2 hours at 37° C. The preparation was phenol/chloroform-extracted, NaOAc was added to 0.3 M, and the preparation was ethanol precipitated. The precipitate was resuspended in 200 to 500 microliters of water and the concentration was estimated by $OD_{260}$ measurement. A working DNA stock was prepared at 10 ng per microliter.

PCR Methods

RAPD PCR

Each 25 μl reaction contained the following:

| | | final conc: |
|---|---|---|
| 2.5 μl buffer | Promega 10X stock | 1X |
| 2.0 μl MgCl₂ | Promega, stock is 25 mM each | 2.0 mM |
| 1.0 μl DNA | @10 ng per microliter | |
| 1.0 μl dNTP mix | @5 mM | 0.2 mM |
| 1.0 μl primer | @~5 mM | 0.2 μM |
| 0.125 μl Taq pol. | @5 units per microliter | |
| 17.5 μl water | | |

A master mix was made containing all the reagents except DNA. 24 μl of the mix was added to each reaction tube. DNA was then added and the tubes were gently mixed by tapping the side. Two drops of mineral oil were added. Tubes were centrifuged briefly to layer oil over the reaction mix.

RAPD PCR, or random amplification of polymorphic DNA using the polymerase chain reaction, is a technique that differs from standard "specific" PCR in several ways. Specific PCR uses two different primers, each usually at least 20 nucleotides in length, at sufficiently high annealing temperatures so that ideally a single band is obtained for each genetic allele. Design of the primer sequences requires DNA sequence information, which may be lacking for new genes or new organisms not previously studied.

RAPD PCR uses single short primers with low annealing temperatures, so that multiple bands are usually seen, no matter what the source of the DNA. No prior sequence information about the organism or the DNA region is needed. The chromosomal location of an amplified fragment is not known; the only characteristic that is important is the correlation of an observed RAPD band with a trait of interest.

RAPD PCR is a good way of finding a large number of variable DNA regions in an organism that has not been widely studied. However, a disadvantage of the RAPD technique is that reproducible results require extreme consistency in reaction conditions, and so RAPD assays are sometimes not reproducible in other laboratories. Our goal has been to locate variable genetic regions using RAPD PCR and then to clone and sequence the variable RAPD fragments and use the sequence information to design locus-specific primer pairs. Successful amplification using locus-specific primer pairs is usually less dependent on reaction conditions and DNA quality.

We screened 250 RAPD primers during the development of the FS-1, FS-2, and FS-3 markers. We began by analyzing 3–4 known individuals of each gypsy moth strain with each primer. The DNA was amplified and the products analyzed on agarose gels as described in the methods section below. Any primers that appeared to amplify fragments which were diagnostic for either Asian or North American moths were used to amplify increasing numbers of samples for as long as the diagnostic pattern held up. The FS-1, FS-2, and FS-3 primers have amplified consistent diagnostic patterns in over 50 Asian and 50 North American moth samples.

Thermal Cycler Conditions, RAPD Primers

The tubes were incubated in a thermal cycler with the following conditions: 94° C. for 2 minutes (initial denaturation step) and 45 cycles of the following three steps: 94° C. for 1 minute, 36° C. for 1 minute, 72° C. for 2 minutes. Reactions were then held at 4° C.

Locus-specific Amplification Methods

Each 25 μl reaction contained the following:

| | | final conc: |
|---|---|---|
| 2.5 μl buffer | Promega 10X stock | 1X |
| 1.0 μl MgCl₂ | Promega, stock is 25 mM each | 1.0 mM |
| 1.0 μl DNA | @10 ng per microliter | |
| 1.0 μl dNTP mix | @5 mM | 0.2 mM |
| 1.0 μl primer | @10 mM | 0.4 μM |
| 1.0 μl primer | @10 mM | 0.4 μM |
| 0.1125 μl Taq pol. | @5 units per microliter | |
| 17.5 μl water | | |

A master mix was made containing all the reagents except DNA. 24 μl of the mix was added to each reaction tube. DNA was then added and the tubes were gently mixed by tapping the side. Two drops of mineral oil were added. Tubes were centrifuged briefly to layer oil over the reaction mix.

Thermal Cycler Conditions, Locus-Specific Primers

The tubes were incubated in a thermal cycler with the following conditions: 94° C. for 2 minutes (initial denaturation step) and 45 cycles of the following three steps: 94° C. for 1 minute, 40°–60° C. for 1 minute (dependent on primer pair characteristics), 72° C. for 1 minute. Reactions were then held at 4° C.

Gel Electrophoresis

About 2–3 microliters of loading dye mix (bromophenol blue dye) were mixed with the sample. 12–13 microliters were loaded per (5 mm wide) lane on a 1.2% agarose gel with TBE buffer. The agarose concentration could be adjusted (0.8 to 4% agarose) depending on the size of the fragment being analyzed. The gel was run at approximately 7 volts per centimeter. For good resolution, the tracking dye was usually run at least 6 cm.

The gel was stained for 30 minutes in TBE containing 0.5 mg per ml ethidium bromide and then photographed.

Primer Sequences

The following RAPD primers were found to amplify differently sized pieces in the Asian and European/North American genomic DNA. RAPD primers (used separately):

FS-1 15' GGA CCC AAC C 3'(SEQ ID NO:3)

FS-2 5' GAG CCC TCC A 3'(SEQ ID NO:6)

FS-3 5' CTT CCG CAG T 3'(SEQ ID NO:7)

Locus-Specific Primer Pair

FS-1-U33: 5' GGA TGG TGG GTG TCG TT 3'(SEQ ID NO:4)

FS-1-L325: 5' GGT TGG TTG ATG ATT AGA TG 3'(SEQ ID NO:5) The calculated optimal annealing temperature for this primer pair was 48.8° C. (using the OLIGO primer analysis program by W. Rychlik).

3. Results

FIG. 1 depicts agarose gel electrophoresis of products of DNA amplification using primer FS-1. Lane 1 is a DNA size marker, lanes 2–9 are Asian gypsy moth samples, lanes 10 and 11 are hybrid moth DNA samples, and lanes 12–19 are European/North American samples. The diagnostic DNA fragments are marked with arrows. Several other non-diagnostic fragments are also visible. Multiple amplified fragments are a normal characteristic of RAPD PCR.

The Asian diagnostic fragment is 700 bp long and is found in Asian samples but not North American/European samples. The North American/European fragment is 590 bp long and is found only in North American/European samples. The FS-1 marker can be used to detect hybrids, as both bands appear in hybrid samples (lanes 10–11 of FIG. 1).

Figure 2:
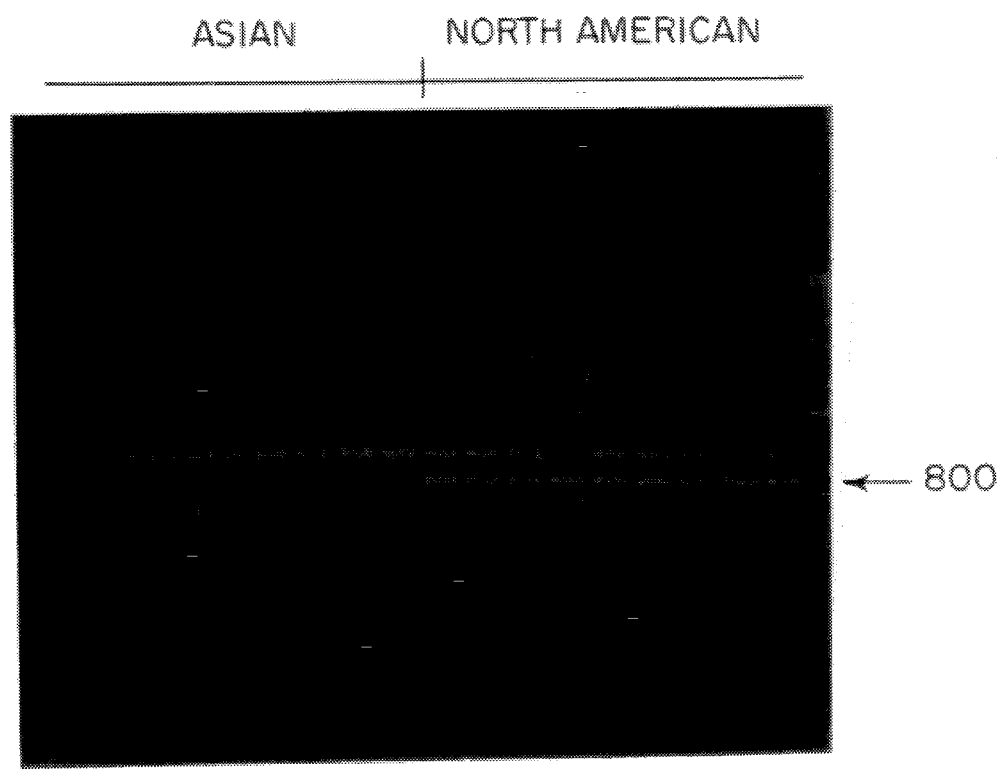
FIG. 2 is a photograph of an agarose gel showing electrophoresis of amplified DNA products created using gypsy moth genomic DNA and primer FS-2.

FIG. 2 depicts agarose gel electrophoresis of products of DNA amplification using primer FS-2. Lanes 1–9 are Asian gypsy moth samples, lanes 10–18 are North American/European samples, and lane 19 is a DNA size marker. The FS-2 marker identifies an 800 bp fragment which is present only in North American/European moth DNA samples. The diagnostic fragment is marked with an arrow. Because the FS-2 marker does not amplify a fragment specific for the Asian strain of gypsy moths, the hybrid moths would show the same banding pattern as the North American gypsy moths.

Figure 3:
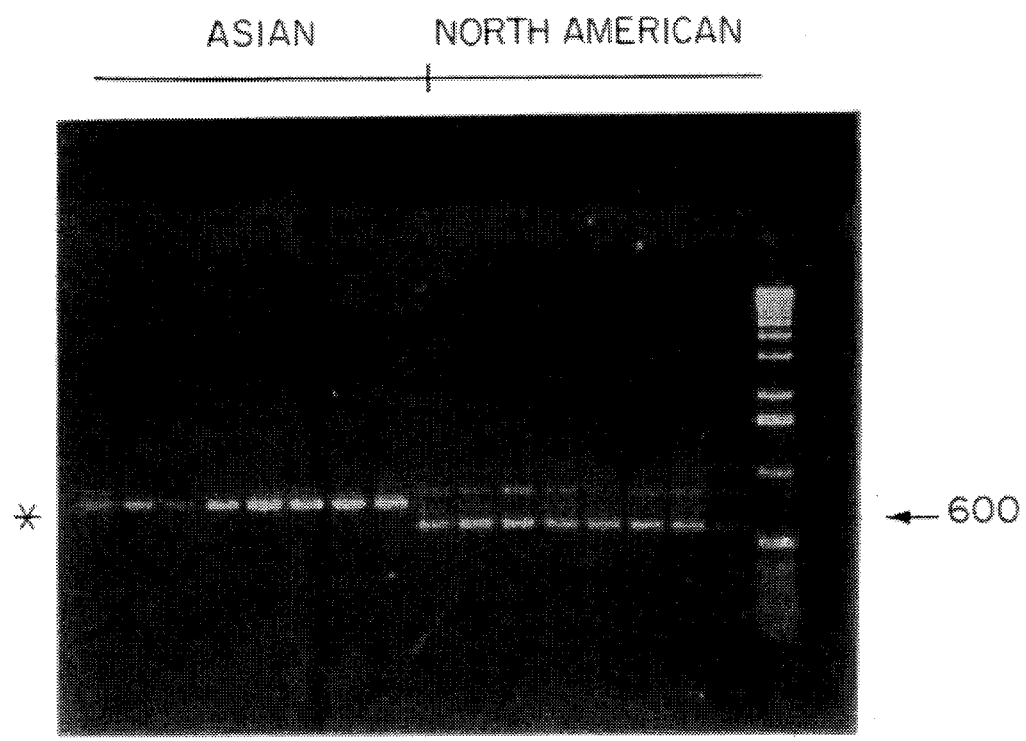
FIG. 3 is a photograph of an agarose gel showing electrophoresis of amplified DNA products created using gypsy moth genomic DNA and primer FS-3.

FIG. 3 depicts agarose gel electrophoresis of products of DNA amplification using primer FS-3. Lanes 1–8 are Asian gypsy moth samples, lanes 9–16 are North American/European samples, and lane 17 is a DNA size marker. The FS-3 marker identifies a 600 bp fragment which is present only in North American/European moth DNA samples. The diagnostic fragment is marked with an arrow. An additional fragment (marked with an *) which appears to be diagnostic for Asian moths occurs in a significant proportion of North American/European samples. Because the FS-3 marker does not amplify a fragment specific for the Asian strain of gypsy moths, the hybrid moths which show the same banding pattern as the North American/European gypsy moths.

We tabulated the results from 108 unknown gypsy moth DNA samples amplified with primers FS-1, FS-2, and FS-3 in Table 1. Results are abbreviated A, Asian; H, Hybrid; and N, North American/European.

TABLE 1

| Sample # | Origin | FS1 | FS2 | FS3 | Sample # | Origin | FS1 | FS2 | FS3 |
|---|---|---|---|---|---|---|---|---|---|
| LD0066 | A-Japan | A | A | A | LD1955 | N-CT | N | N | A |
| LD0067 | A-Japan | A | A | A | LD1956 | N-CT | N | N | N |
| LD0068 | A-Japan | A | A | A | LD1957 | N-CT | N | N | N |
| LD0069 | A-Japan | A | A | A | LD1958 | N-CT | N | N | N |
| LD0098 | A-Russia | A | A | A | LD1959 | N-CT | N | N | N |
| LD0099 | A-Russia | A | A | A | LD0048 | N-MA | N | N | N |
| LD0100 | A-Russia | A | A | A | LD0049A | N-MA | N | N | N |
| LD0101 | A-Russia | A | A | A | LD0049B | N-MA | N | N | N |
| LD1898 | A-Russia | A | A | A | LD0057 | N-MA | N | N | N |
| LD1899 | A-Russia | A | A | A | LD0064 | N-MA | N | N | N |
| LD1900 | A-Russia | A | A | A | LD0065 | N-MA | N | N | N |
| LD1901 | A-Russia | A | A | A | LD0080 | N-MI | N | N | A |
| LD1902 | A-Russia | A | A | A | LD0081 | N-MI | — | N | N |
| LD1903 | A-Russia | A | A | A | LD0082 | N-MI | N | N | N |
| LD1940 | A-Russia | — | A | A | LD0083 | N-MI | N | N | N |
| LD1941 | A-Russia | — | A | A | LD0084 | N-MI | N | N | N |
| LD1942 | A-Russia | A | A | — | LD0085 | N-MI | N | N | N |
| LD1943 | A-Russia | A | A | — | LD0006 | N-NJ std | — | N | N |
| LD1944 | A-Russia | A | A | A | LD0008 | N-NJ std | N | N | N |
| LD1945 | A-Russia | A | A | A | LD0009 | N-NJ std | N | N | N |
| LD1946 | A-Russia | A | N | A | LD0010 | N-NJ std | N | N | N |
| LD1947 | A-Russia | A | A | N | LD0070 | N-OH | N | N | N |
| LD1948 | A-Russia | A | A | A | LD0071 | N-OH | N | N | N |
| LD1949 | A-Russia | A | A | A | LD0072 | N-OH | N | N | N |
| LD1950 | A-Russia | A | A | N | LD0078 | N-OH | H | — | N |
| LD1951 | A-Russia | A | A | A | LD0079 | N-OH | N | N | A |
| LD1952 | A-Russia | A | A | A | LD0026 | N-PA | N | N | N |
| LD1953 | A-Russia | A | A | A | LD0027 | N-PA | N | N | N |
| LD1954 | A-Russia | A | A | N | LD0028 | N-PA | N | N | N |
| LD0001 | A-ship | A | A | A | LD0029 | N-PA | N | N | N |
| LD0002 | A-ship | A | A | A | LD1924 | N-PA | N | N | N |
| LD0003 | A-ship | A | A | A | LD1925 | N-PA | N | N | N |
| LD0004 | A-ship | A | A | A | LD1926 | N-PA | N | N | N |
| LD0005 | A-ship | A | A | — | LD1927 | N-PA | N | N | N |
| LD0030 | A-ship | A | A | A | LD1928 | N-PA | N | N | N |
| LD0031 | A-ship | A | A | A | LD1929 | N-PA | N | N | N |
| LD0032 | A-ship | A | A | A | LD1930 | N-PA | N | N | N |
| LD0033 | A-ship | A | A | A | LD1931 | N-PA | N | N | N |
| LD0033B | A-ship | A | A | — | LD0074 | N-WV | N | — | N |
| LD0034 | A-ship | A | A | A | LD0075 | N-WV | N | N | N |
| LD0036 | A-ship | A | — | A | LD0076 | N-WV | N | N | N |
| LD0037 | A-ship | A | A | A | LD0077 | N-WV | N | — | A |
| LD0038 | A-ship | A | A | A | LD1912 | N-WV | N | N | N |
| LD0039A | A-ship | A | A | A | LD1913 | N-WV | H | N | N |
| LD0040 | A-ship | A | A | A | LD1932 | N-WV | N | N | N |
| LD0041 | A-ship | A | A | A | LD1933 | N-WV | N | N | N |
| LD0042 | A-ship | A | A | A | LD1934 | N-WV | N | N | N |
| LD0043 | A-ship | A | A | — | LD1935 | N-WV | N | N | N |
| LD0044 | A-ship | A | A | N | LD1936 | N-WV | N | N | N |
| LD0045 | A-ship | A | A | A | LD1937 | N-WV | N | N | N |
| LD0046 | A-ship | A | A | A | LD1938 | N-WV | N | N | N |
| LD0047 | A-ship | A | A | A | LD1960 | N-WV | — | N | N |
| | | | | | LD1961 | N-WV | N | N | N |
| | | | | | LD1962 | N-WV | N | N | N |
| | | | | | LD1963 | N-WV | N | N | N |
| | | | | | LD1964 | N-WV | N | N | — |

The success rate of primers FS-1, FS-2, and FS-3 when used to analyze the gypsy moth DNA samples described in Table 1 is tabulated below in Table 2:

TABLE 2

| | Proportion correctly identified: | | |
|---|---|---|---|
| | FS-1 | FS-2 | FS-3 |
| Asian | 50/50 or 100% | 50/51 or 98% | 43/47 or 91% |
| North American | 51/53 or 96% | 53/53 or 100% | 50/54 or 94% |

The results in Table 2 demonstrate that when analyzing gypsy moth DNA samples with markers FS-1, FS-2, or FS-3, the accuracy rates are approximately 98%, 99% and 92% respectively. When all three markers are used on each sample and all three are in agreement, a very high accuracy rate of approximately 99.9998% is achieved.

Hybrid gypsy moth DNA samples amplified with locus-specific primers FS1-U33 and FS1-L325 produced diagnostic results. Hybrids were produced from crosses of a Russian mother by Massachusetts father (RxMA), Russian mother by North Carolina father (RxNC), Massachusetts mother by Russian father (MAxR), and North Carolina mother by Russian father (NCxR). These hybrids are all Asian-North American/European crosses. Results are abbreviated A, Asian; H, Hybrid, and N, North American. The hybrid result is indicated by the presence of both the 700 bp Asian band and the 590 bp North American band (see FIG. 1). Table 3 below tabulates the results.

The success rate of primer FS-1 when used to identify hybrid moths is 15/20 or 75%. Because the primary purpose of these markers will be to identify the introduction of the Asian genotype into North America/European, the misidentification of hybrids as pure Asians will not be a serious problem. When used to indicate the presence of the Asian genotype in known hybrids, the success rate for FS-1 is 19/20 or 95%.

TABLE 3

| Specimen # | Cross | Results |
|---|---|---|
| LD094 | RxMA | H |
| LD095 | RxMA | A |
| LD096 | MAxR | H |
| LD097 | MAxR | H |
| LD134 | MAxR | A |
| LD135 | MAxR | A |
| LD136 | MAxR | H |
| LD137 | MAxR | H |
| LD181 | MAxR | H |
| LD182 | MAxR | H |
| LD184 | MAxR | H |
| LD189 | NCxR | H |
| LD190 | NCxR | H |
| LD191 | NCxR | H |
| LD192 | NCxR | H |

4. Development of Locus-Specific Primers

The diagnostic DNA fragments amplified from Asian and North American/European gypsy moths with primer FS-1 were further characterized by cloning and DNA sequence determination. The two FS-1 fragments are nearly identical except that the North American fragment is lacking a 110 bp region which is present in the Asian fragments FIG. 4 compares the two sequences. SEQ ID NO:1 is the Asian DNA sequence and SEQ ID NO:2 is the North American/European DNA sequence. Extended primer sequences (FS1-U33 and FS1-L325) were selected in regions lacking nucleotide polymorphisms. Both FS1-U33 and FS1-L325 are indicated on FIG. 4 and at SEQ ID NOs:4 and 5. The extended primer sequences amplify fewer interfering fragments than the FS-1 RAPD primer and have proven to provide more reproducible results when used in other laboratories.

FIG. 4 depicts the alignment of FS-1 diagnostic fragment nucleotide sequences. The consensus sequences were based on the analysis of 4 Asian and 2 North American/European individuals. Ambiguous positions are indicated by the standard IUPAC codes. The positions of the extended primer sequences are indicated above and below the aligned sequences.

Figure 5:
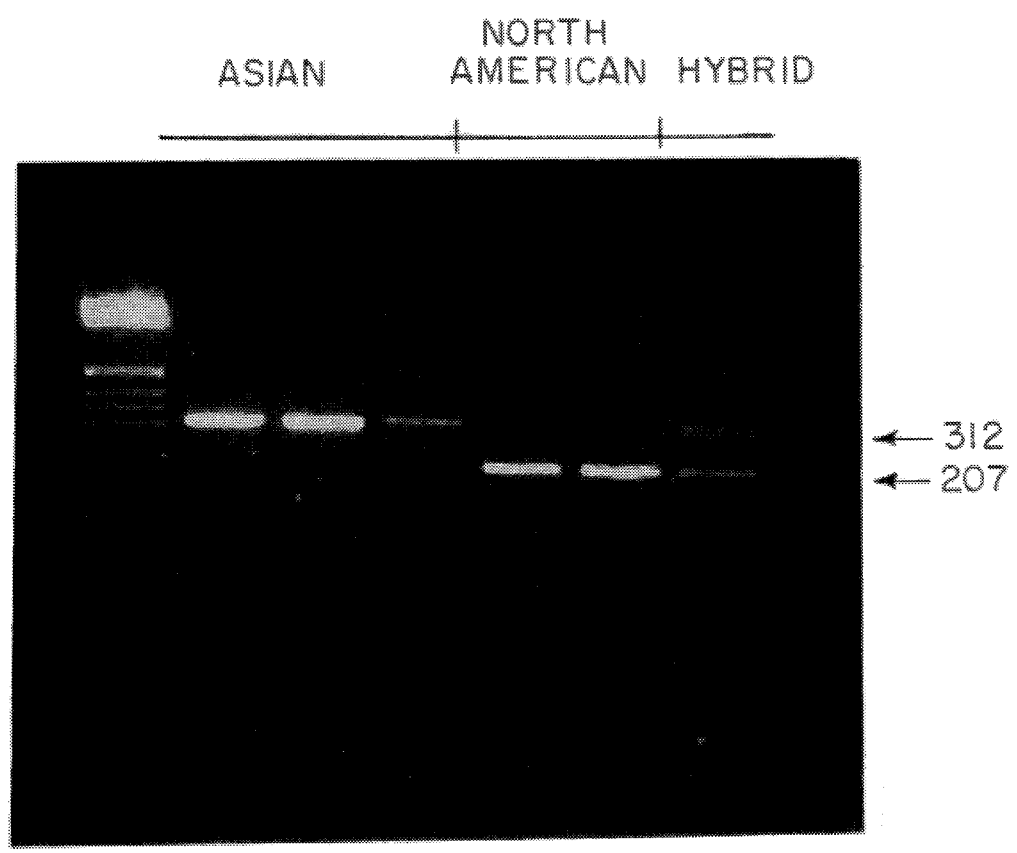
FIG. 5 is a photograph of an agarose gel showing electrophoresis of amplified DNA products created using gypsy moth genomic DNA and primers FS1-U33 and FS1-L325.

FIG. 5 depicts agarose gel electrophoresis of products of DNA amplification using the locus-specific primers FS1-U33 and FS1-L325. Lane 1 is a DNA size marker, lanes 2-4 are Asian gypsy moth samples, lanes 5 and 6 are North American/European moth DNA samples, and lane 7 is a hybrid sample.

The fragment sizes using this primer set are 312 bp for the Asian marker and 207 bp for the North American/European marker. An additional, slower migrating band appears upon amplification of hybrid individuals. This is a heteroduplex between the 312 and 207 bp fragments, produced by denaturation followed by annealing during the final PCR cycles. The diagnostic DNA fragments are marked with arrows.

Results from Asian and North American gypsy moth DNA samples amplified with locus-specific primers FS1-U33 and FS1-L325 are tabulated in Table 4. Results are abbreviated A, Asian; H, Hybrid; and N, North American/European.

TABLE 4

| Specimen # | Asian Origin | Result | Specimen # | North American Origin | Result |
|---|---|---|---|---|---|
| LD022 | A-Japan | A | LD049A | N-MA | N |
| LD023 | A-Japan | A | LD049B | N-MA | N |
| LD024 | A-Japan | A | LD057 | N-MA | N |
| LD025 | A-Japan | A | LD064 | N-MA | N |
| LD066 | A-Japan | A | LD065 | N-MA | N |
| LD067 | A-Japan | A | LD139 | N-MA | N |
| LD068 | A-Japan | A | LD140 | N-MA | N |
| LD069 | A-Japan | A | LD141 | N-MA | N |
| LD161 | A-Russia | A | LD197 | N-MA | N |
| LD188 | A-Russia | A | LD198 | N-MA | N |
| LD208 | A-Russia | A | LD199 | N-MA | N |
| LD098 | A-Russia | A | LD200 | N-MA | N |
| LD100 | A-Russia | A | LD212 | N-MA | N |
| LD101 | A-Russia | A | LD213 | N-MA | N |
| LD209 | A-Russia | A | LD214 | N-MA | N |
| LD210 | A-Russia | A | LD215 | N-MA | N |
| LD211 | A-Russia | A | LD138 | N-MA | N |
| LD158 | A-Russia | A | LD172 | N-NC | N |
| LD159 | A-Russia | A | LD142 | N-NC | N |
| LD160 | A-Russia | A | LD143 | N-NC | N |
| LD187 | A-Russia | A | LD144 | N-NC | N |
| LD001 | A-ship | A | LD145 | N-NC | N |
| LD003 | A-ship | A | LD169 | N-NC | N |
| LD004 | A-ship | A | LD194 | N-NC | N |
| LD005 | A-ship | A | LD195 | N-NC | N |
| LD031 | A-ship | A | LD196 | N-NC | N |
| LD032 | A-ship | A | LD170 | N-NC | N |
| LD034 | A-ship | A | LD171 | N-NC | N |
| LD040 | A-ship | A | LD008 | N-NJ | N |
| LD044 | A-ship | A | LD009 | N-NJ | N |
| LD045 | A-ship | A | LD078 | N-OH | H |
| | | | LD071 | N-OH | N |
| | | | LD070 | N-OH | N |
| | | | LD072 | N-OH | N |
| | | | LD073 | N-OH | N |
| | | | LD026 | N-PA | N |
| | | | LD029 | N-PA | N |
| | | | LD027 | N-PAt | N |
| | | | LD028 | N-PAt | N |
| | | | LD075 | N-WV | N |
| | | | LD074 | N-WV | N |

The success rate of locus-specific primers FS1-U33 and FS1-L325 when used to analyze gypsy moth DNA samples is tabulated in Table 5.

TABLE 5

| Proportion correctly identified: | | |
|---|---|---|
| Asian | 32/32 | 100% |
| North American | 41/42 | 98% |

Hybrid gypsy moth DNA samples were amplified with locus-specific primers FS1-U33 and FS1-L325. The hybrids were produced from crosses of a Russian mother by Massachusetts father (RxMA), Russian mother by North Carolina father (RxNC), Massachusetts mother by Russian father (MAxR), and North Carolina mother by Russian father (NCxR). Table 6, below, tabulates the results. Results are abbreviated A, Asian; H, Hybrid; and N, North American.

The success rate of locus-specific primers FS1-U33 and FS1-L325 when used to identify hybrid moths was 35/39 or 90%. Since the primary purpose of these markers will be to identify the introduction of the Asian genotype into North America, the mis-identification of hybrids as pure Asians will not be a serious problem. When used to indicate the presence of the Asian genotype in known hybrids the success rate is 38/39 or 97%.

TABLE 6

| Specimen # | Cross | Result | Sample # | Cross | Results |
|---|---|---|---|---|---|
| LD094 | RxMA | H | LD162 | RxMA | H |
| LD095 | RxMA | A | LD163 | RxMA | H |
| LD096 | MAxR | H | LD164 | RxMA | H |
| LD097 | MAxR | N | LD165 | RxMA | H |
| LD134 | MAxR | A | LD173 | MAxR | H |
| LD135 | MAxR | A | LD174 | MAxR | H |
| LD136 | MAxR | H | LD176 | MAxR | H |
| LD137 | MAxR | H | LD204 | NCxR | H |
| LD146 | RxNC | H | LD205 | NCxR | H |
| LD147 | RxNC | H | LD206 | NCxR | H |
| LD148 | RxNC | H | LD207 | NCxR | H |
| LD149 | RxNC | H | LD216 | NCxR | H |
| LD150 | RxNC | H | LD217 | NCxR | H |
| LD151 | RxNC | H | LD218 | NCxR | H |
| LD152 | RxNC | H | LD219 | NCxR | H |
| LD153 | RxNC | H | LD220 | RxNC | H |
| LD154 | RxMA | H | LD221 | RxNC | H |
| LD155 | RxMA | H | LD222 | RxNC | H |
| LD156 | RxMA | H | LD223 | RxNC | H |
| LD157 | RxMA | H | | | |

We claim:
1. A method for determining the genotype of a gypsy moth comprising the steps of
   (a) isolating genomic DNA from a candidate gypsy moth;
   (b) exposing the DNA to an oligonucleotide primer selected from the group consisting of SEQ ID NO:3, SEQ ID NO:6, SEQ ID NO:7, and SEQ ID NOs:4 and 5;
   (c) comparing the amplification products of step (b) to determine the presence or absence of diagnostic fragments obtained from exposing genomic DNA obtained from control Asian and North American/European gypsy moths to the primer or primers selected in step (b) under conditions permitting amplification of genomic DNA; and
   (d) determining a genotype identity of the candidate moth according to which control sample has amplified fragments similar to those produced in step (b).

2. The method of claim 1 wherein the comparison of step (c) is by electrophoresing the amplified DNA.

3. The method of claim 1 wherein the oligonucleotide primer is SEQ ID NO:3 and the amplified DNA from the control Asian moths is 700 bp as determined by gel electrophoresis and from control North American/European moths is 590 bp as determined by gel electrophoresis.

4. The method of claim 1 wherein the oligonucleotide primer is SEQ ID NO:6 and the amplified DNA from the control North American/European moths is 800 bp as determined by agarose gel electrophoresis and the 800 bp as determined by agarose gel electrophoresis fragment is absent in control Asian moth samples.

5. The method of claim 1 wherein the oligonucleotide primer is SEQ ID NO:7 and the amplified DNA from the control North American/European moths is 600 bp as determined by agarose gel electrophoresis and the 600 bp as determined by agarose gel electrophoresis fragment is absent from control Asian moth samples.

6. The method of claim 1 wherein the oligonucleotide primers are SEQ ID NOs:4 and 5 and the amplified DNA from control Asian moths is 312 bp as determined by gel electrophoresis and from control North American/European moths is 207 bp as determined by gel electrophoresis.

7. A method of obtaining DNA primers for determining the genotype of candidate moths comprising the steps of:
   (a) obtaining genomic gypsy moth DNA from Asian and North American/European moths;
   (b) obtaining fragment FS-2 or FS-3 from North American/European DNA by exposing the DNA to primers selected from the group consisting of SEQ ID NOs: 6 and 7 wherein fragment FS-2 is a fragment of 800 bp as measured by agarose gel electrophoresis amplified by primer SEQ ID NO:6 from North American/European gypsy moth DNA and wherein fragment FS-3 is a fragment of 600 bp as measured by agarose gel electrophoresis amplified by primer SEQ ID NO:7 from North American/European gypsy moth DNA; and
   (c) analyzing the DNA sequence of the fragments obtained in step (b) to obtain a primer which amplifies a product of 800 bp or 600 bp as determined by agarose gel electrophoresis in North American/European gypsy moth DNA samples.

8. A method of obtaining DNA primers for determining the genotype of candidate moths comprising the step of:
   analyzing the DNA sequence of fragment FS-1 obtained from Asian and North American/European gypsy moths to obtain a primer which amplifies a product of 312 bp as measured by agaraose gel electrophoresis in Asian gypsy moth DNA samples and a product of 207 bp as measured by agarose gel electrophoresis in North American/European gypsy moth DNA samples,
   wherein fragment FS-1 is a fragment of 700 bp as measured by agarose gel electrophoresis amplified by primer SEQ ID NO:3 from Asian gypsy moth DNA and 590 bp as measured by agarose gel electrophoresis amplified by primer SEQ ID NO:3 from North American/European gypsy moth DNA.

9. The method of claim 8 wherein the FS-1 fragment sequences are SEQ ID NOs:1 and 2.

10. A purified preparation of an oligonucleotide primer with the DNA sequence of SEQ ID NO:4.

11. A purified preparation of an oligonucleotide primer with the DNA sequence of SEQ ID NO:5.

12. A method for determining the genotype of a gypsy moth comprising the steps of
   (a) isolating genomic DNA from a candidate gypsy moth;
   (b) exposing the DNA to an oligonucleotide primer selected from the group consisting of SEQ ID NO:3, SEQ ID NO: 6, SEQ ID NO:7, and SEQ ID NOs:4 and 5 and sequences sufficiently similar to SEQ ID NOs:4 and 5 such that an amplification product of identical size as determined by 1.2% agarose gel electrophoresis is obtained, wherein said exposure is under conditions permitting amplification of the genomic DNA;

(c) examining the amplification products of step (b) for the presence or absence of diagnostic fragments obtained from exposing genomic DNA obtained from control Asian and North American/European gypsy moths to the primer or primers selected in step (b) under conditions permitting amplification of genomic DNA; and (d) assigning a genotype identity to the candidate moth according to which control sample has amplified fragments similar to those produced in step (b).

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 696 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GGACCCAACC  CGTCTGATCA  GYATGGTATA  GCGGATGGTG  GGTGTCGTTA  ARGACGTTTA       60

AAATGTATAT  AACATCAATG  TCAGAGAAAG  AAAACTCAAC  ATAAAGTATG  CCAACTCGWC      120

TGRCYAKCTT  GATATAGTAG  GTCAATTKCT  ACCCCATTAT  GGAAGGAGGT  TCAAGRGCAG      180

CACTGAGACA  GAGATTGAAC  TGTGATCATG  AATTATCAGG  ATCAGATGAA  TCTAAAACAA      240

ATACCTAACC  AAAAATTGGA  ATAAACTAAT  TTTAYGGTAA  TTTTAAGGYT  AATAATCATA      300

ATTCATAAGC  AAATTATTCC  ACAACATCTR  ATCATCAACC  AACCGCCYCA  AACAACAGAA      360

CAAATRAGCA  ACACGTCGAT  GTCCTCTCCG  GAATGACAAT  GATTATTGTA  ACAGCCTCAT      420

AAACCGGCAT  TATTGTGAGC  GCACTGTATT  TATACGCCAT  AGCAATTATC  GGTCGTAACT      480

GCCGCATCGA  TCTTCGTCGA  TAATTGCCTT  TGTAAACATG  AGTTATTGTT  CCATCTGAAC      540

TAATTAGTGT  ATGTTATTAG  GTTAAGGGTG  ACATTTTGAA  GTYATACTAC  TTCTGACACT      600

TTAGGGRAAA  AACATCATCG  GGCCGACCAC  TGAAGACAAG  TTACTCTGCA  CCGATGGTCG      660

GCTCAACGAT  GAAGGCGACG  TGTCACGGTT  GGGTCC                                  696
```

( 2 ) INFORMATION FOR SEQ ID NO:2:

(i) SEQUENCE CHARACTERISTICS:
  (A) LENGTH: 590 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:2:

| | | | | | | |
|---|---|---|---|---|---|---|
| GGACCCAACC | CGTCTGATCA | GTATGGTATA | GGGGATGGTG | GGTGTCGTTA | AAGACGTTTA | 60 |
| AAATGTATAC | AGCAGTACTG | AGACAGAGAT | TGAACTGTGA | TCATGAATTA | TCAGGATCAG | 120 |
| ATGAATCTAA | AACAAATACC | TAACCAAAAA | TTGGAATAAM | CTAATTTTAT | GGTAATTTTA | 180 |
| AGGCTAATAA | TCATAATTCA | TAAGCAAATT | ATTCCACAAC | ATCTAATCAT | CAACCAACCG | 240 |
| CCTCAAACAA | CAGAACAAAT | AAGCAACACG | TCGATGTCCT | CTCCGGAATG | ACAATGATTA | 300 |
| TYGTARCAGC | CTCATAAACC | GGCATTATTG | TGANNGNACT | GTATTTATAC | NNATAGCAAT | 360 |
| TATCGGTCGT | AACTGCCGCA | TCGATCTTCG | TCGATAATTG | CCTTGTGAAA | CATGAGTTAT | 420 |
| TGTTCCATAT | GAACTAATTA | GTGTATGTTA | TTAGGTTAAG | GGTGACATTT | TGAAGTTATA | 480 |
| CTACTTCTGA | CACTTTAGGG | NAAAACATC | ATCGGGCCGA | CCACTGAAGA | CAAGTTACTC | 540 |
| TGCACCGATG | GTCGGCTCAA | CGATGAAGGC | GACGTGTCAC | GGTTGGGTCC | | 590 |

(2) INFORMATION FOR SEQ ID NO:3:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: oligonucleotide (xi) SEQUENCE DESCRIPTION: SEQ ID NO:3:

GGACCCAACC                                                              10

(2) INFORMATION FOR SEQ ID NO:4:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: oligonucleotide (xi) SEQUENCE DESCRIPTION: SEQ ID NO:4:

GGATGGTGGG TGTCGTT                                                      17

(2) INFORMATION FOR SEQ ID NO:5:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: oligonucleotide (xi) SEQUENCE DESCRIPTION: SEQ ID NO:5:

GGTTGGTTGA TGATTAGATG                                                   20

(2) INFORMATION FOR SEQ ID NO:6:

(i) SEQUENCE CHARACTERISTICS:

(A) LENGTH: 10 base pairs
(B) TYPE: nucleic acid
(C) STRANDEDNESS: single
(D) TOPOLOGY: linear (ii) MOLECULE TYPE: oligonucleotide (xi) SEQUENCE DESCRIPTION: SEQ ID NO:6:

GAGCCCTCCA 10

(2) INFORMATION FOR SEQ ID NO:7:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: oligonucleotide (xi) SEQUENCE DESCRIPTION: SEQ ID NO:7:

CTTCCGCAGT 10